United States Patent
Yamada et al.

(10) Patent No.: US 10,126,121 B2
(45) Date of Patent: Nov. 13, 2018

(54) METHOD OF MEASURING SCANNING CHARACTERISTICS OF OPTICAL SCANNING APPARATUS AND CHART FOR MEASURING SCANNING CHARACTERISTICS USED IN SAME

(71) Applicant: OLYMPUS CORPORATION, Tokyo (JP)

(72) Inventors: Masashi Yamada, Tokyo (JP); Atsuyoshi Shimamoto, Tokyo (JP); Soichiro Koshika, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/789,390

(22) Filed: Oct. 20, 2017

(65) Prior Publication Data
US 2018/0038686 A1 Feb. 8, 2018

Related U.S. Application Data

(63) Continuation of application No. PCT/JP2015/002239, filed on Apr. 24, 2015.

(51) Int. Cl.
*G01B 11/26* (2006.01)
*G01M 11/00* (2006.01)
(Continued)

(52) U.S. Cl.
CPC .......... *G01B 11/26* (2013.01); *A61B 1/00057* (2013.01); *A61B 1/00172* (2013.01);
(Continued)

(58) Field of Classification Search
CPC .... G01B 11/26; G01B 15/004; G01B 15/002; G01B 11/272; G01B 11/27
(Continued)

(56) References Cited

U.S. PATENT DOCUMENTS

2012/0078137 A1\* 3/2012 Mendels ................ A61B 5/205
600/584
2014/0022365 A1 1/2014 Yoshino

FOREIGN PATENT DOCUMENTS

JP 2003021752 A 1/2003
JP 2005090962 A 4/2005
(Continued)

OTHER PUBLICATIONS

International Preliminary Report on Patentability together with the Written Opinion from related International Application No. PCT/JP2015/002239 dated Nov. 2, 2017.
(Continued)

*Primary Examiner* — Md M Rahman
(74) *Attorney, Agent, or Firm* — Scully, Scott, Murphy & Presser, P.C.

(57) ABSTRACT

A method of measuring scanning characteristics of an optical scanning apparatus allows measurement of scanning characteristics of an actuator. The method includes bringing a tip of the optical scanning apparatus and a chart for measuring scanning characteristics closer together and irradiating illumination light with the actuator in a non-driven state, separating the tip and the chart for measuring scanning characteristics by a predetermined distance while maintaining the relative orientations thereof, and adjusting a drive signal of the actuator so that a scanning area of the illumination light on the chart for measuring scanning characteristics can form a desired shape. At least one of an angle of deviation and a viewing angle is measured using an irradiation position of the illumination light on the chart for measuring scanning characteristics.

9 Claims, 16 Drawing Sheets

(51) Int. Cl.
*G02B 23/26* (2006.01)
*G02B 26/10* (2006.01)
*G02B 23/24* (2006.01)
*A61B 1/00* (2006.01)

(52) U.S. Cl.
CPC ......... *G01M 11/00* (2013.01); *G02B 23/2469* (2013.01); *G02B 23/26* (2013.01); *G02B 26/10* (2013.01); *G02B 26/101* (2013.01); *G02B 26/103* (2013.01)

(58) Field of Classification Search
USPC ....................................................... 356/138
See application file for complete search history.

(56) References Cited

FOREIGN PATENT DOCUMENTS

| | | |
|---|---|---|
| JP | 2014018556 A | 2/2014 |
| JP | 5469280 B1 | 4/2014 |
| JP | 2014090780 A | 5/2014 |
| JP | 2014147462 A | 8/2014 |
| JP | 2015020003 A | 2/2015 |

OTHER PUBLICATIONS

International Search Report dated Jul. 21, 2015 issued in PCT/JP2015/002239.

* cited by examiner

METHOD OF MEASURING SCANNING CHARACTERISTICS OF OPTICAL SCANNING APPARATUS AND CHART FOR MEASURING SCANNING CHARACTERISTICS USED IN SAME

CROSS-REFERENCE TO RELATED APPLICATION

The present application is a Continuing Application based on International Application PCT/JP2015/002239 filed on Apr. 24, 2015, the entire disclosure of which is incorporated herein by reference.

TECHNICAL FIELD

This disclosure relates to a method of measuring scanning characteristics of an optical scanning apparatus and to a chart for measuring scanning characteristics used in the method.

BACKGROUND

One known optical scanning apparatus is, for example, a scanning endoscope that vibrates an emission end of an optical fiber in two dimensions with an actuator, scans an object being observed (irradiated portion) spirally with illumination light passing from the optical fiber through an illumination optical system, and generates an image by detecting signal light, such as scattered light, from the object being observed. In such a scanning endoscope, the scanning position on the object being observed and the pixel position in the generated image need to be matched accurately.

As one method for doing so, patent literature 1 (PTL 1), for example, discloses a method to detect the scanning trajectory of the scanning endoscope with a position sensitive detector (PSD) and to calibrate the driving voltage applied to the actuator so that the scanning trajectory can become a predetermined standard scanning trajectory. In greater detail, the calibration method of PTL 1 sets the frequency of the driving voltage so as to maximize the amplitude of the scanning trajectory, sets a phase difference of the driving voltage in two dimensions so that the scanning trajectory can become a substantially true circle, and sets the maximum amplitude of the driving voltage in two dimensions so that the magnitude and shape of the scanning trajectory can be within predetermined ranges.

CITATION LIST

Patent Literature

PTL 1: JP 2014-147462 A

SUMMARY

A method according to this disclosure is a method of measuring scanning characteristics of an optical scanning apparatus that drives an actuator and scans illumination light in two dimensions, the method including:

a first step, with the actuator in a non-driven state, of bringing a tip, that emits the illumination light, of the optical scanning apparatus and a chart for measuring scanning characteristics closer together and irradiating the chart for measuring scanning characteristics with the illumination light;

a second step of separating the tip and the chart for measuring scanning characteristics by a predetermined distance while maintaining relative orientations of the tip and the chart for measuring scanning characteristics from the first step; and a third step of adjusting a drive signal of the actuator so that a scanning area of the illumination light on the chart for measuring scanning characteristics can form a desired shape, wherein at least one of an angle of deviation and a viewing angle is measured using an irradiation position of the illumination light on the chart for measuring scanning characteristics.

In the method of measuring scanning characteristics,
the illumination light may be emitted from an optical fiber,
the actuator may vibrate an emission end of the optical fiber in an x-direction and a y-direction both orthogonal to an extending direction of the emission end and may scan the illumination light in two dimensions, and
the third step may adjust a frequency, an amplitude, and a phase difference of an X drive signal that drives the actuator in the x-direction and a Y drive signal that drives the actuator in the y-direction.

In the method of measuring scanning characteristics,
the chart for measuring scanning characteristics may include concentric viewing angle index patterns, and
the third step may adjust the X drive signal and the Y drive signal so that a scanning trajectory of the illumination light can be inscribed in a desired one of the viewing angle index patterns.

In the method of measuring scanning characteristics,
after the first step, a bright spot of the illumination light may be placed substantially at a center of the viewing angle index patterns before the second step, and
after the second step, the angle of deviation may be measured using the viewing angle index patterns and the bright spot of the illumination light positioned on the chart for measuring scanning characteristics.

In the method of measuring scanning characteristics, the viewing angle may be measured using the viewing angle index patterns.

The method of measuring scanning characteristics may further include:
a fourth step, after the third step, of substantially matching a center of the scanning area of the illumination light to a center of the viewing angle index patterns of the chart for measuring scanning characteristics, wherein
in the fourth step, the viewing angle is measured using the viewing angle index patterns.

In the method of measuring scanning characteristics,
the chart for measuring scanning characteristics may include a coordinate index pattern indicating coordinate positions, and
the angle of deviation may be measured using the following equation, where a distance between the tip of the optical scanning apparatus and the chart for measuring scanning characteristics is $L_1$ and a coordinate position of a bright spot of the illumination light on the chart for measuring scanning characteristics is $(x_1, y_1)$ in the first step, and
a distance between the tip of the optical scanning apparatus and the chart for measuring scanning characteristics is $L_2$ and a coordinate position of a bright spot of the illumination light on the chart for measuring scanning characteristics is $(x_2, y_2)$ in the second step.

$$\theta = \arctan\left(\frac{\sqrt{(x_2-x_1)^2+(y_2-y_1)^2}}{|L_2-L_1|}\right)$$

In the method of measuring scanning characteristics, the chart for measuring scanning characteristics may be imaged by an imaging apparatus and displayed on a display.

In the method of measuring scanning characteristics, the chart for measuring scanning characteristics may be imaged by an imaging apparatus, and the scanning characteristics may be calculated automatically by a calculator using image information obtained from the imaging apparatus.

In the method of measuring scanning characteristics, the optical scanning apparatus may be a scanning endoscope.

A chart for measuring scanning characteristics according to this disclosure is used in a method of measuring scanning characteristics of an optical scanning apparatus that drives an actuator and scans illumination light in two dimensions, the chart comprising:

concentrically formed viewing angle index patterns.

In the chart for measuring scanning characteristics, the viewing angle index patterns may be concentric circles.

DETAILED DESCRIPTION

Scanning endoscopes are required to have a large viewing angle (such as 90°). In a scanning endoscope, however, the central axis of the optical fiber and the optical axis of the illumination optical system might not match when the optical fiber is in a non-vibrating state (non-scanning state) depending on factors such as assembly error of the actuator or the illumination optical system. In this case, the illumination light emitted from the endoscope is inclined relative to the standard emission direction, which is the extending direction of the insertion tip. If this inclination (angle of deviation) is large, the desired viewing angle might not be obtained by a 2D scan of the illumination light with the actuator. Therefore, for example during a manufacturing test of the endoscope, scanning characteristics such as the angle of deviation and the viewing angle of the actuator are preferably measured. The angle of deviation also changes over time and for other such reasons. Hence, the scanning characteristics are preferably measured at appropriate times.

The technique disclosed in PTL 1, however, calibrates the driving voltage of the actuator so as to obtain a standard scanning trajectory that is centered on the irradiation position in a non-vibrating state of the optical fiber and makes no mention whatsoever of measurement of scanning characteristics such as the angle of deviation and the viewing angle. Such scanning characteristics are not limited to a scanning endoscope and are also important elements in, for example, a laser scanning microscope that vibrates an emission end of an optical fiber with an actuator in two dimensions and scans a sample through an objective lens with laser light from the optical fiber.

In light of these considerations, this disclosure provides a method of measuring scanning characteristics of an optical scanning apparatus, and a chart for measuring scanning characteristics used in the method, that allow measurement of scanning characteristics of an actuator.

Embodiments of this disclosure are described below with reference to the drawings.

Embodiment 1

Figure 1:
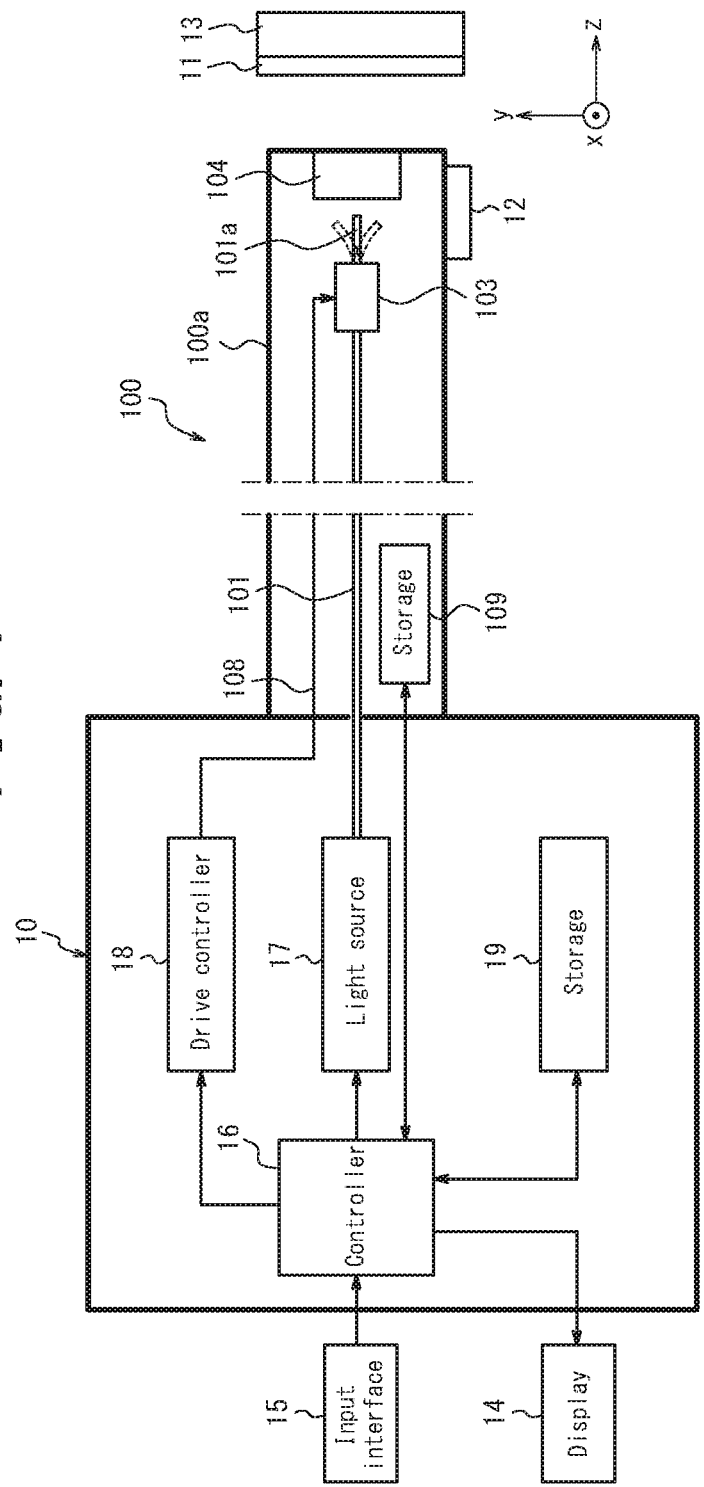
FIG. 1 is a block diagram illustrating the main configuration of an apparatus for measuring scanning characteristics according to Embodiment 1.

FIG. 1 is a block diagram illustrating the main configuration of an apparatus for measuring scanning characteristics according to Embodiment 1. The apparatus for measuring scanning characteristics according to this embodiment is for measuring the scanning characteristics of a scanning endoscope (scope) 100. The apparatus for measuring scanning characteristics includes a measurement apparatus body 10, a chart 11 for measuring scanning characteristics, a Z stage 12, and an XY stage 13. As necessary, the measurement apparatus body 10 includes a display 14 and an input interface 15, such as a keyboard, a mouse, or a touch panel.

The scanning endoscope 100 is detachably connected to the measurement apparatus body 10 by a connector or the like. An insertion tip 100a of the scanning endoscope 100 is held on the Z stage 12 and is disposed by the Z stage 12 displaceably in the extending direction (z-direction) of the insertion tip 100a.

Figure 2:
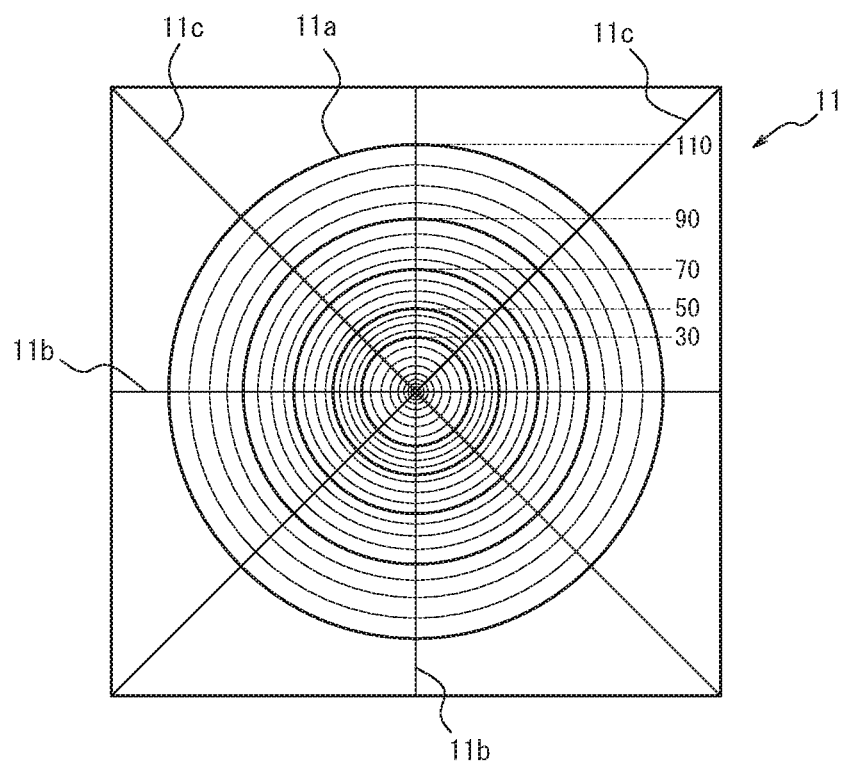
FIG. 2 is an expanded plan view of the chart for measuring scanning characteristics in FIG. 1.

The chart 11 for measuring scanning characteristics is, for example, constituted by a substantially square flat plate member, is held on the XY stage 13 approximately in parallel to a plane orthogonal to the z-direction, and is disposed by the XY stage 13 displaceably in the x-direction and the y-direction, which are both orthogonal to the z-direction. As illustrated in the expanded plan view in FIG. 2, a plurality of concentric circular viewing angle index patterns 11a centered substantially on the center of the square, for example, are formed on the chart 11 for measuring scanning characteristics. In FIG. 2, the viewing angle index patterns 11a for viewing angles of 30°, 50°, 70°, 90°, and 110° are indicated in bold, and viewing angle index patterns 11a at a 5° pitch are indicated by thin circles between the bold circles. Lines 11b passing through the center of the viewing angle index patterns 11a and corresponding to the x-direction and the y-direction and diagonals 11c inclined by 45° relative to the lines 11b are also formed in FIG. 2.

The Z stage 12 and the XY stage 13 may be operated manually or operated automatically by the measurement apparatus body 10.

An optical fiber 101 for illumination and optical fiber 102 for receiving light (see FIG. 3) are disposed inside the scanning endoscope 100 and extend from the base end joined to the measurement apparatus body 10 to the insertion tip 100a. Illumination light from the measurement apparatus body 10 can enter the optical fiber 101 for illumination while the scanning endoscope 100 is connected to the measurement apparatus body 10.

Figure 3:
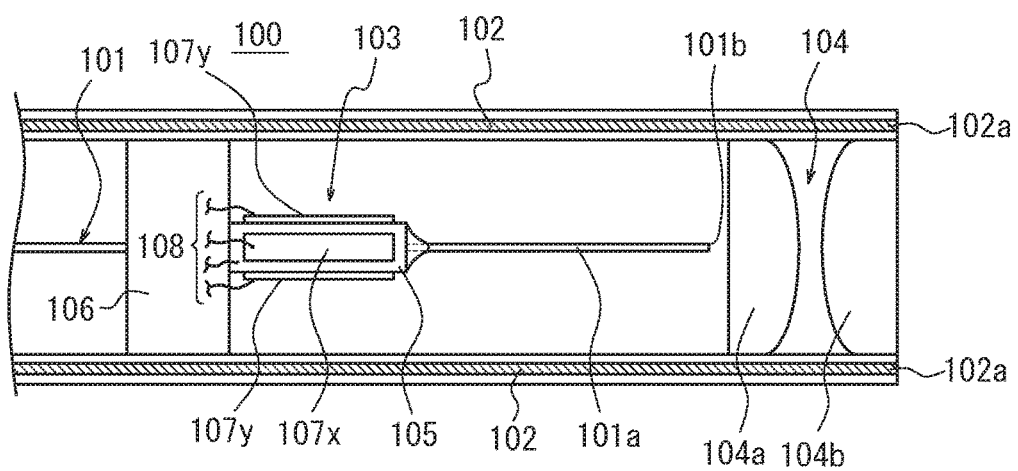
FIG. 3 is a partially expanded cross-sectional diagram of the insertion tip of the scanning endoscope in FIG. 1.

As illustrated in the partially expanded cross-sectional diagram of FIG. 3, an actuator 103 and an illumination optical system 104 are mounted in the insertion tip of the scanning endoscope 100. The actuator 103 includes a ferrule 105 that is a fiber holder to hold an emission end 101a of the optical fiber 101 for illumination by the emission end 101a passing through the ferrule 105. The optical fiber 101 for illumination is adhered to the ferrule 105. The end of the ferrule 105 opposite from an emission end face 101b of the optical fiber 101 for illumination is joined to a support 106 so that the ferrule 105 can be supported at one end by the support 106 to allow oscillation. The optical fiber 101 for illumination extends through the support 106.

The ferrule 105 is, for example, made of a metal such as nickel. The ferrule 105 may be formed in any shape, such as a quadrangular prism or a cylinder. Piezoelectric elements 107x and 107y respectively corresponding to the x-direction and the y-direction are mounted on the ferrule 105. Only one of the piezoelectric elements 107x is illustrated in FIG. 3. The piezoelectric elements 107x and 107y are rectangular, with the long sides in the z-direction. The piezoelectric elements 107x and 107y each have an electrode formed on both surfaces in the thickness direction and are each configured to be capable of expanding and contracting in the z-direction upon voltage being applied in the thickness direction via the opposing electrodes.

Corresponding wiring cables 108 are connected to the electrode surfaces of the piezoelectric elements 107x and 107y opposite the electrode surfaces adhered to the ferrule 105. Similarly, corresponding wiring cables 108 are connected to the ferrule 105, which acts as a common electrode for the piezoelectric elements 107x and 107y. To the two piezoelectric elements 107x opposite each other in the x-direction, an in-phase, AC X drive signal is applied from the measurement apparatus body 10 through the corresponding wiring cables 108. Similarly, to the two piezoelectric elements 107y opposite each other in the y-direction, an in-phase, AC Y drive signal is applied from the measurement apparatus body 10 through the corresponding wiring cables 108.

With this configuration, when one of the two piezoelectric elements 107x expands, the other contracts, causing the ferrule 105 to vibrate by bending in the x-direction. Similarly, when one of the two piezoelectric elements 107y expands, the other contracts, causing the ferrule 105 to vibrate by bending in the y-direction. As a result, the x-direction vibration and y-direction vibration are combined, so that the ferrule 105 is deflected integrally with the emission end 101a of the optical fiber 101 for illumination. Accordingly, upon illumination light entering the optical fiber 101 for illumination from the measurement apparatus body 10, the illumination light emitted from the emission end face 101b is deflected in two dimensions.

The optical fibers 102 for receiving light are disposed as a bundle at the outer circumferential portion of the scanning endoscope 100. A non-illustrated detection lens may also be disposed at the entrance tip 102a side of the optical fibers 102 for receiving light. While the scanning endoscope 100 is connected to the observation apparatus body for endoscopic observation, reflected light, fluorescent light, or other light is yielded by the object being observed (object being illuminated) as a result of irradiation with the illumination light from the optical fiber 101 for illumination. The optical fibers 102 for receiving light capture this light as signal light and guide the signal light to the observation apparatus body.

The example of the illumination optical system 104 in FIG. 3 is configured by two projection lenses 104a, 104b. The projection lenses 104a, 104b are configured so as to concentrate illumination light, emitted from the emission end face 101b of the optical fiber 101 for illumination, on a predetermined focal position. The illumination optical system 104 is not limited to two projection lenses 104a, 104b and may be configured as a single lens or as three or more lenses.

As illustrated in FIG. 1, the scanning endoscope 100 further includes a storage 109. ID information of the scanning endoscope 100 is stored in the storage 109. As necessary, the below-described drive signal information, scanning characteristics information, and the like are stored in the storage 109. During endoscopic observation using the scanning endoscope 100, the information stored in the storage 109 is read by the observation apparatus body as necessary while the scanning endoscope 100 is connected to the observation apparatus body.

The measurement apparatus body 10 in FIG. 1 includes a controller 16 that controls operations of the apparatus overall, a light source 17, a drive controller 18, and a storage 19.

The light source 17 includes a light source such as a laser diode or a diode-pumped solid-state (DPSS) laser. As during endoscopic observation of color images with the scanning endoscope 100, the light source 17 may be configured with a plurality of lasers that emit blue, green, and red laser light, or the light source 17 may be configured with a single laser for measurement of scanning characteristics. Light emitted from the light source 17 is incident on the optical fiber 101 for illumination of the scanning endoscope 100.

The drive controller 18 supplies a drive signal over the wiring cables 108 to the actuator 103 of the scanning endoscope 100. The storage 19 stores information such as control programs of the measurement apparatus body 10. The storage 19 may also function as a working memory. The storage 19 may be an internal memory of the measurement apparatus body 10 or may be a portable storage medium (such as a memory card) removable from the measurement apparatus body 10.

Figure 4:
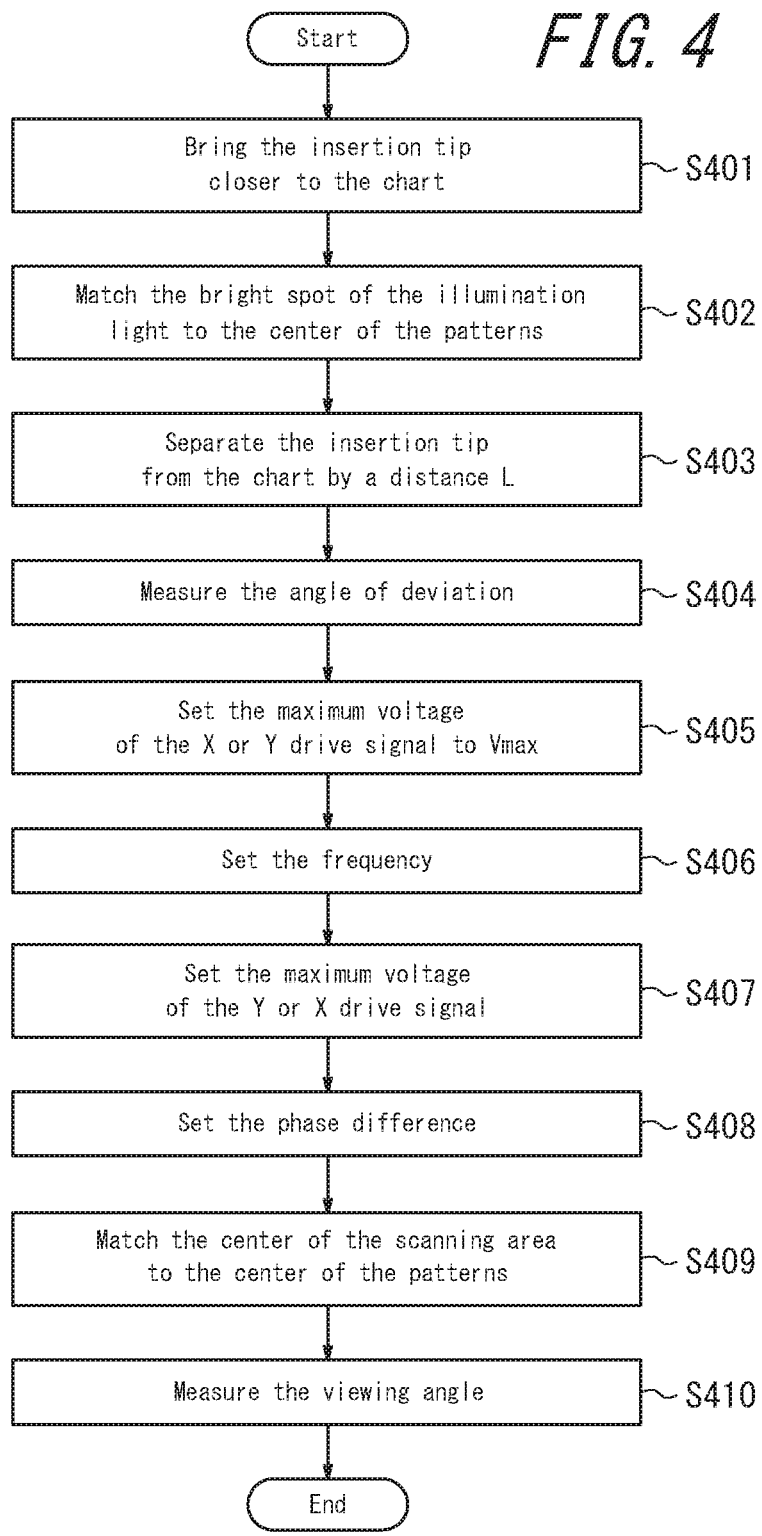
FIG. 4 is a flowchart illustrating the main processing for measurement of scanning characteristics by the apparatus for measuring scanning characteristics in FIG. 1.

FIG. 4 is a flowchart illustrating the main processing for measurement of scanning characteristics of the scanning endoscope 100 by the apparatus for measuring scanning characteristics according to this embodiment. In the following description, the scanning endoscope 100 targeted for measurement is assumed to scan illumination light spirally. To prepare for measurement, the base end of the scanning endoscope 100 targeted for measurement is connected to the measurement apparatus body 10, and the insertion tip 100a is held on the Z stage 12. The chart 11 for measuring scanning characteristics is held on the XY stage 13.

In this state, the insertion tip 100a is displaced in the z-direction by the Z stage 12 to be brought closer to the chart 11 for measuring scanning characteristics (step S401). The insertion tip 100a is preferably brought close to the chart 11 for measuring scanning characteristics and positioned near the illumination optical system 104. The actuator 103 is in a non-driven state. The light source 17 is driven by the controller 16, and the chart 11 for measuring scanning characteristics is displaced by the XY stage 13 within the zy plane. As illustrated schematically in FIG. 5, a bright spot SP of the illumination light irradiated from the insertion tip 100a onto the chart 11 for measuring scanning characteristics is thus positioned at the center of the concentric circular viewing angle index patterns 11a (step S402).

Figure 6:
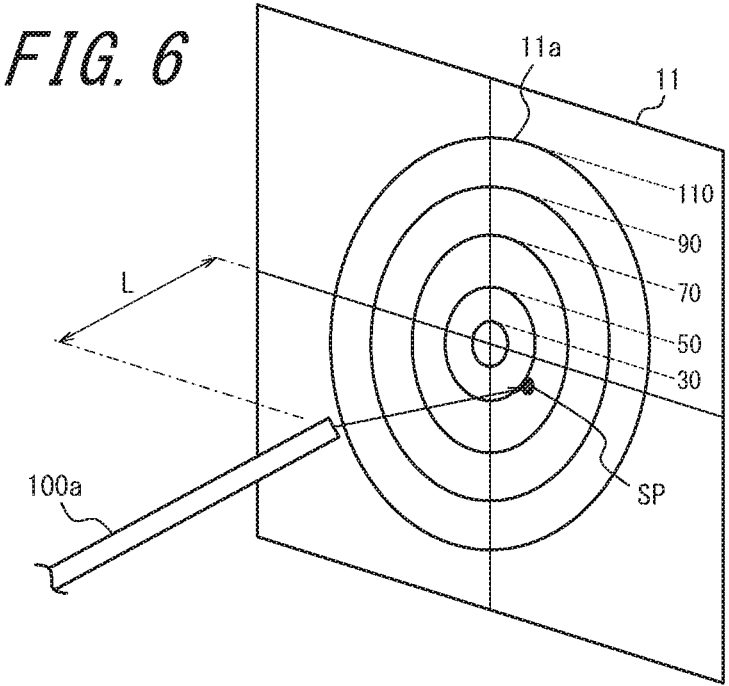
FIG. 6 illustrates step S403 of FIG. 4.

Next, while maintaining the relative orientations of the insertion tip 100a and the chart 11 for measuring scanning characteristics, the insertion tip 100a is displaced in the z-direction by the Z stage 12 to place the insertion tip 100a at a predetermined distance L away from the chart 11 for measuring scanning characteristics, as illustrated schematically in FIG. 6 (step S403). The predetermined distance L is, for example, the distance from the end of the insertion tip 100a to the object being observed during endoscopic observation by the scanning endoscope 100 targeted for measurement and may, for example, be 10 mm. In this state, the measurer measures the angle of deviation using the bright spot SP of the illumination light, located on the chart 11 for measuring scanning characteristics, and the viewing angle index patterns 11a (step S404). The illumination light may be irradiated continually during displacement of the insertion tip 100a or may be suspended during displacement and then resumed after displacement. In the case of FIG. 6, since the bright spot SP contacts the viewing angle index patterns 11a at a viewing angle of 50°, the angle of deviation is half of the viewing angle, i.e. 25°.

Subsequently, with the light source 17 in a driven state, the drive controller 18 is driven by the controller 16, and the maximum voltage of the X drive signal or the Y drive signal applied to the piezoelectric elements 107x or 107y of the actuator 103 in FIG. 3 is set to the upper limit voltage Vmax (step S405). Here, for the sake of convenience, the maximum voltage of the X drive signal is first set to the upper limit voltage Vmax. During the setting process, the controller 16 gradually increases the voltage of the X drive signal from 0 V to the upper limit voltage Vmax and then scans the chart 11 for measuring scanning characteristics linearly with the illumination light. The voltage of the Y drive signal is 0 V, i.e. the Y drive signal is off.

Figure 7:
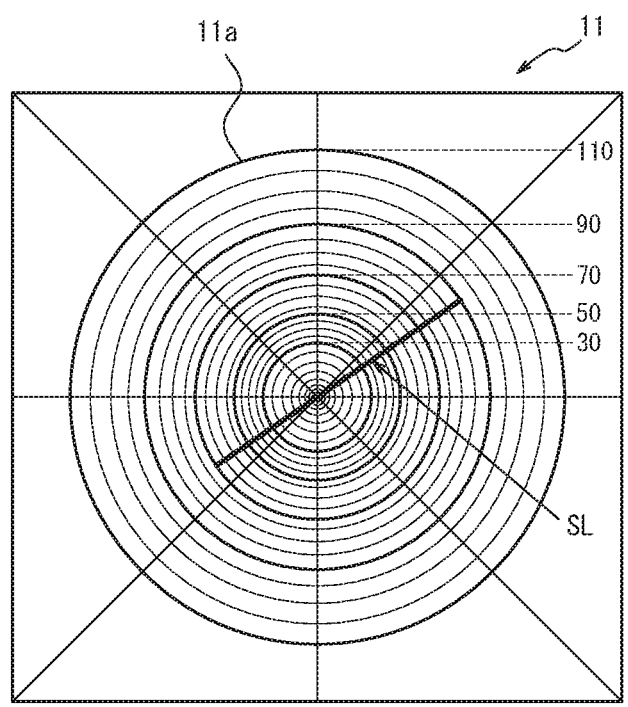
FIG. 7 illustrates step S405 of FIG. 4.

At this time, at the upper limit voltage Vmax or less, if the scanning trajectory formed on the chart 11 for measuring scanning characteristics exceeds the viewing angle index pattern 11a for a desired viewing angle, such as a viewing angle of 90°, then the controller 16 increases or decreases the frequency of the X drive signal. In other words, the frequency of the X drive signal is shifted from the resonance frequency of the moving part that includes the actuator 103. As a result, as illustrated in FIG. 7, the scanning trajectory SL of illumination light formed on the chart 11 for measuring scanning characteristics is inscribed within the viewing angle index pattern 11a for a desired viewing angle. In FIG. 7, the direction of the scanning trajectory SL is shifted in the x-direction of the chart 11 for measuring scanning characteristics because the insertion tip 100a rotates about the z-axis when held on the Z stage 12. This shift poses no problem for measurement of scanning characteristics.

Next, the maximum voltage of the X drive signal is fixed at the upper limit voltage Vmax, and the frequency of the X drive signal is adjusted and set by the controller 16 so that the scanning trajectory SL can be inscribed within the viewing angle index pattern 11a for a desired viewing angle (step S406).

Figure 8:
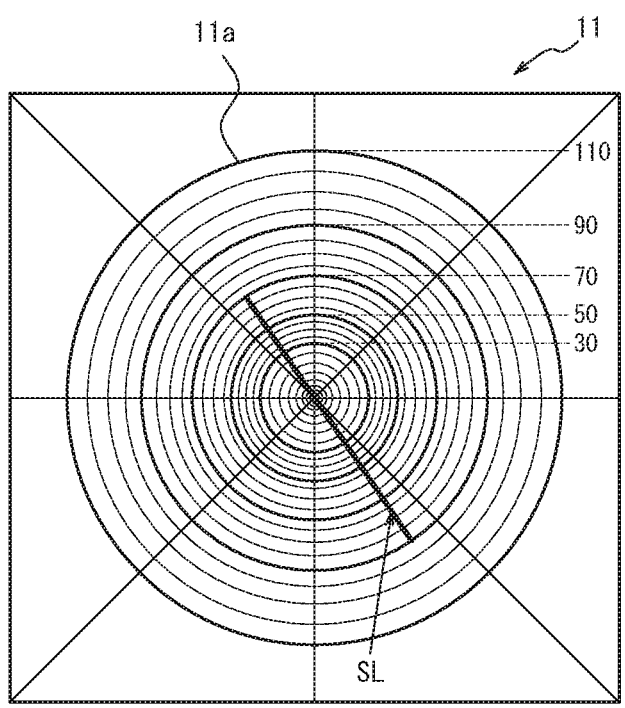
FIG. 8 illustrates step S407 of FIG. 4.

Subsequently, the X drive signal is turned off, and the maximum voltage of the Y drive signal is set (step S407). During the setting process, the controller 16 sets the frequency of the Y drive signal to the frequency of the X drive signal set in step S406 and gradually increases the voltage from 0 V. As illustrated in FIG. 8, the scanning trajectory SL of illumination light formed on the chart 11 for measuring scanning characteristics is then inscribed within the viewing angle index pattern 11a for a desired viewing angle, and the voltage at this time as set as the maximum voltage of the Y drive signal (step S407).

In step S407, when the maximum voltage of the Y drive signal exceeds the upper limit voltage Vmax, the processes to set the X drive signal and the Y drive signal are executed in reverse. In other words, the settings in steps S405 to S407 are reset, the maximum voltage of the Y drive signal is set to the upper limit voltage Vmax in step S405, the frequency of the Y drive signal is set in step S406, and the maximum voltage of the X drive signal is set in step S407.

Figure 9:
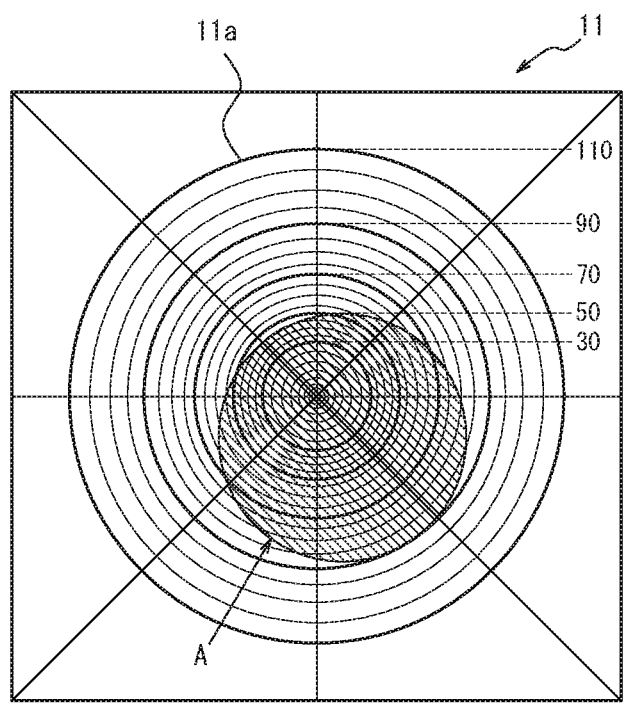
FIG. 9 illustrates step S408 of FIG. 4.

Next, the phase of the X drive signal and the Y drive signal, i.e. the phase difference between these drive signals, is set (step S408). In this setting process, the controller 16 first applies an X drive signal and a Y drive signal that have a phase difference of 90° and that gradually increase and decrease to the piezoelectric elements 107x and 107y of the actuator 103. As a result, the chart 11 for measuring scanning characteristics is scanned spirally by the illumination light, and the scanning area A illustrated in FIG. 9 is formed. Here, when the scanning area A does not have the desired circularity (for example, 90% or greater), the controller 16 adjusts the phase of the X or Y drive signal to change the phase difference from 90°, for example 1° at a time, until obtaining the desired circularity. The phase difference for which the scanning area A is inscribed in the viewing angle index pattern 11a for the desired viewing angle and which yields the desired circularity is thus determined. The circularity is defined as the (minor axis radius)/(major axis radius) of an ellipse.

Figure 10:
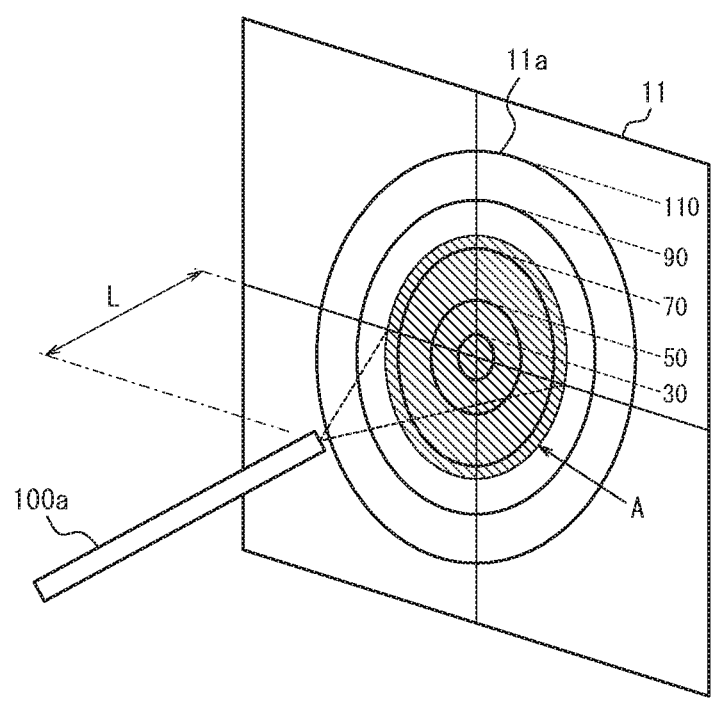
FIG. 10 illustrates step S409 of FIG. 4.

Subsequently, the chart 11 for measuring scanning characteristics is displaced in the xy plane by the XY stage 13, and as illustrated in FIG. 10, the center of the scanning area A is substantially matched to the center of the viewing angle index pattern 11a of the chart 11 for measuring scanning characteristics (step S409). In this state, the measurer measures the viewing angle using the viewing angle index patterns 11a and the scanning area A formed on the chart 11 for measuring scanning characteristics (step S410). In the case of FIG. 10, the viewing angle is approximately 75°.

Figure 5:
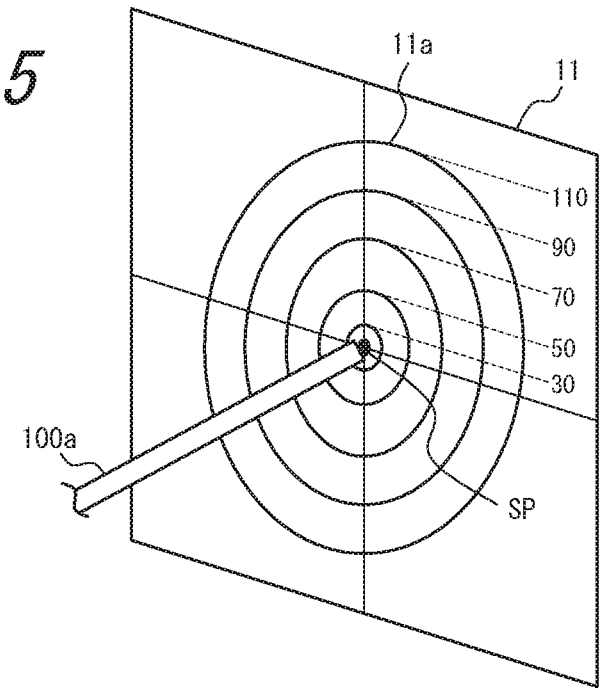
FIG. 5 illustrates step S402 of FIG. 4.

In the flowchart in FIG. 4, step S401 corresponds to the first step, step S403 corresponds to the second step, steps S405 to S408 correspond to the third step, and step S409 corresponds to the fourth step. In FIGS. 5, 6, and 10, a portion of the viewing angle index patterns 11a and the diagonals 11c are omitted from the chart 11 for measuring scanning characteristics to clarify the illustrations.

In this way, the scanning characteristics of the scanning endoscope 100 can be measured in an appropriate driving state of the actuator 103, i.e. a driving state such that the maximum voltage of the X drive signal and the Y drive signal do not exceed the upper limit voltage Vmax, and such that the scanning area A with the desired shape is obtained. When the resulting measured angle of deviation and viewing angle do not satisfy product specifications, the scanning endoscope 100 can, for example, be deemed defective.

The scanning characteristics information on the measured angle of deviation and viewing angle and the drive signal information on the maximum voltage, frequency, and phase difference of the X drive signal and the Y drive signal can be stored in the storage 19. When the scanning endoscope 100 is deemed non-defective, the controller 16 may transfer these pieces of information from the storage 19 to the storage 109 of the scanning endoscope 100 and store the pieces of information in the storage 109. With this approach, by reading the scanning characteristics information and the drive signal information from the storage 109 when the scanning endoscope 100 is connected to the observation apparatus body and endoscopic observation is actually performed, the angle of deviation and the viewing angle can be displayed on the display to notify the user, and the actuator 103 of the scanning endoscope 100 can be driven in an appropriate driving state by the observation apparatus body.

In the configuration illustrated in FIG. 1, the insertion tip 100*a* of the scanning endoscope 100 could extend in the z-direction and be held displaceably in the x-direction and the y-direction by the XY stage, and the chart 11 for measuring scanning characteristics could be held displaceably in the z-direction by the Z stage. Furthermore, one of the insertion tip 100*a* and the chart 11 for measuring scanning characteristics could be fixed while the other is held displaceably in three axial directions by an XYZ stage.

Embodiment 2

Figure 11:
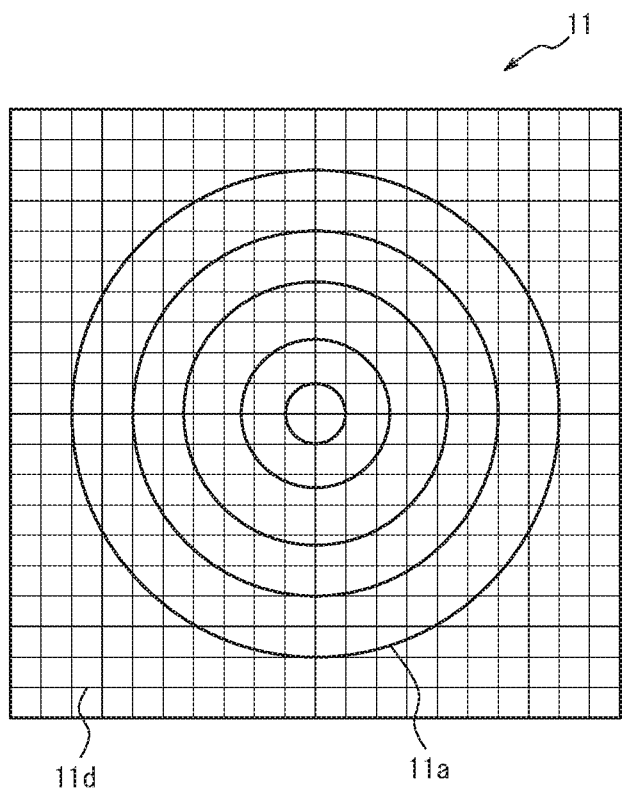
FIG. 11 is a plan view of the chart for measuring scanning characteristics used in an apparatus for measuring scanning characteristics according to Embodiment 2.

FIG. 11 is a plan view of the chart for measuring scanning characteristics used in an apparatus for measuring scanning characteristics according to Embodiment 2. The chart 11 for measuring scanning characteristics illustrated in FIG. 11 includes a plurality of concentric circular viewing angle index patterns 11*a* and a grid-shaped coordinate index pattern 11*d* indicating coordinate positions.

Figure 12:
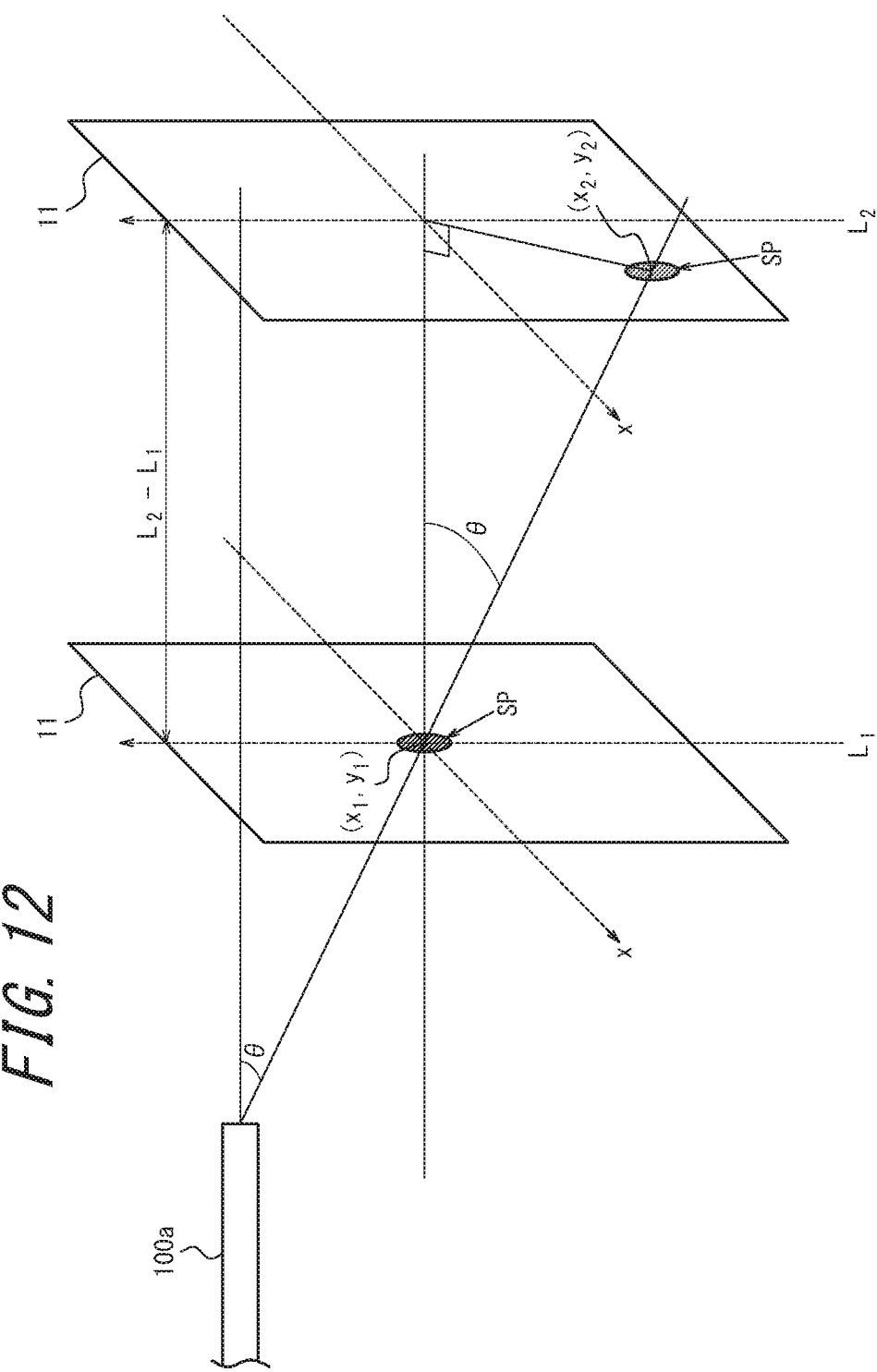
FIG. 12 illustrates an example of a method of measuring the angle of deviation with the chart for measuring scanning characteristics in FIG. 11.

By using the chart 11 for measuring scanning characteristics in FIG. 11, for example the angle of deviation of the scanning endoscope 100 can be measured in the following way in the apparatus for measuring scanning characteristics illustrated in FIG. 1. First, the insertion tip 100*a* and the chart 11 for measuring scanning characteristics are brought closer together with step S401 in FIG. 4, and in this state, illumination light is irradiated onto the chart 11 for measuring scanning characteristics. In this embodiment, the insertion tip 100*a* and the chart 11 for measuring scanning characteristics are not absolutely required to be close together. As illustrated in FIG. 12, the distance between the insertion tip 100*a* and the chart 11 for measuring scanning characteristics at this time is taken as $L_1$, and the coordinate position of the bright spot SP of the illumination light on the chart 11 for measuring scanning characteristics is taken as $(x_1, y_1)$.

Next, with step S403 of FIG. 4, the insertion tip 100*a* is separated from the chart 11 for measuring scanning characteristics while maintaining the relative orientations of the insertion tip 100*a* and the chart 11 for measuring scanning characteristics. As illustrated in FIG. 12, the distance between the insertion tip 100*a* and the chart 11 for measuring scanning characteristics at this time is taken as $L_2$, and the coordinate position of the bright spot SP of the illumination light on the chart 11 for measuring scanning characteristics is taken as $(x_2, y_2)$.

By the above operations, the angle of deviation θ of the scanning endoscope 100 can be calculated with the following equation.

$$\theta = \arctan\left(\frac{\sqrt{(x_2 - x_1)^2 + (y_2 - y_1)^2}}{|L_2 - L_1|}\right)$$

By using the chart 11 for measuring scanning characteristics in FIG. 11 to measure the angle of deviation θ, the operation to position the bright spot SP of the illumination light at the center of the concentric circular viewing angle index patterns 11*a* in step S402 of FIG. 4 can be omitted. Accordingly, the operation to measure the angle of deviation is easier. Of course, when measuring the angle of deviation, the bright spot SP of the illumination light may be positioned at the center of the concentric circular viewing angle index patterns 11*a*. The viewing angle can also be measured in the same way as described in FIG. 4.

Embodiment 3

Figure 13:
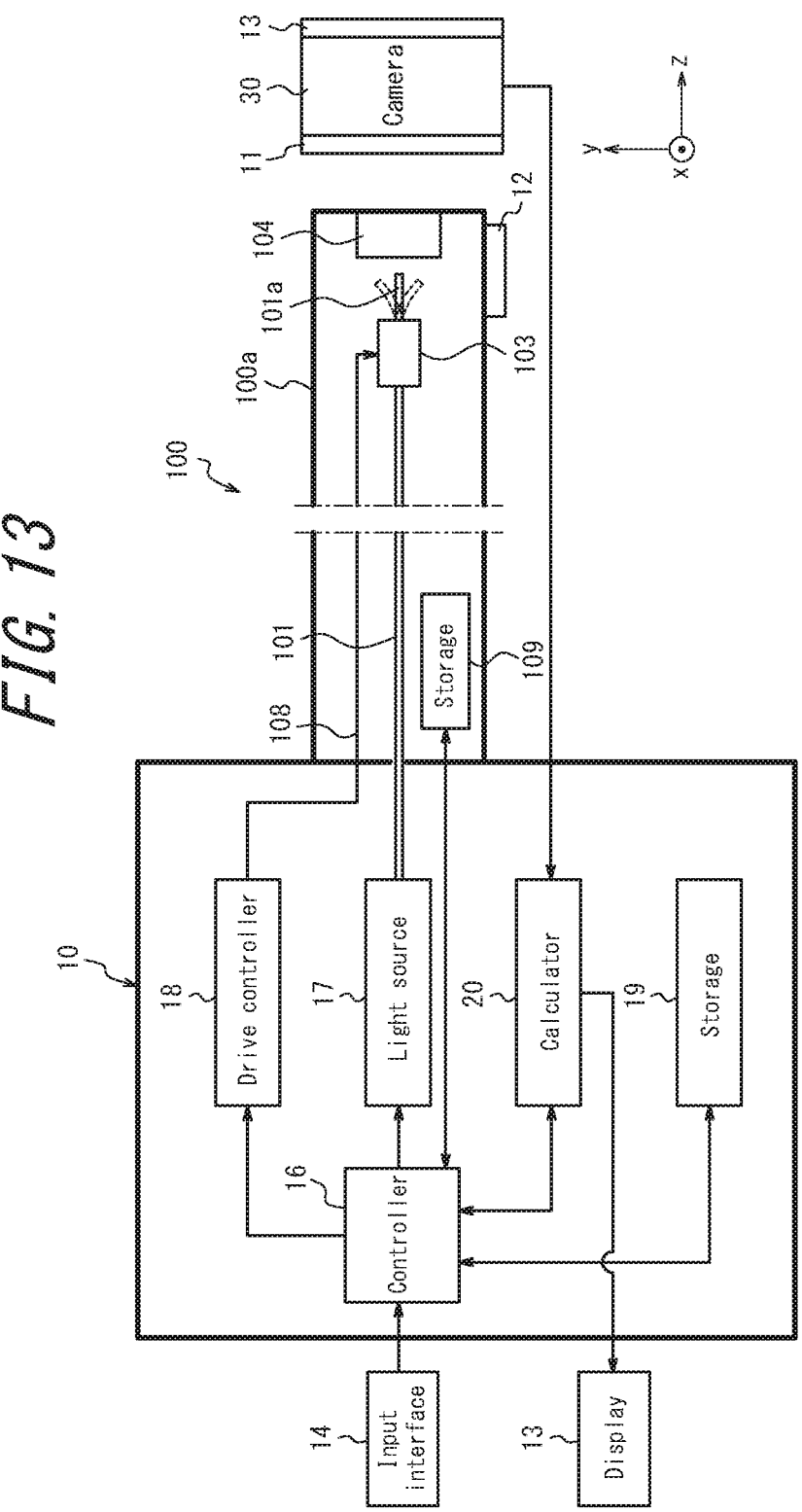
FIG. 13 is a block diagram illustrating the main configuration of an apparatus for measuring scanning characteristics according to Embodiment 3.

FIG. 13 is a block diagram illustrating the main configuration of an apparatus for measuring scanning characteristics according to Embodiment 3. The apparatus for measuring scanning characteristics according to this embodiment has the configuration illustrated in FIG. 1, with the measurement apparatus body 10 further including a calculator 20. The chart 11 for measuring scanning characteristics is also attached to a camera (imaging apparatus) 30. The camera 30 is arranged displaceably in the x-direction and the y-direction integrally with the chart 11 for measuring scanning characteristics by an XY table 13. The camera 30 images the chart 11 for measuring scanning characteristics and inputs the resulting image information to the calculator 20 of the measurement apparatus body 10. The chart 11 for measuring scanning characteristics is configured so that the viewing angle index patterns 11*a* and the bright spot of the illumination light can be imageable by the camera 30. Since the remaining configuration is similar to that of the apparatus for measuring scanning characteristics illustrated in FIG. 1, the differences are described below.

In this embodiment, after performing steps S401 and S402 in FIG. 4, an image of the chart 11 for measuring scanning characteristics having the bright spot SP illustrated in FIG. 5 is captured with the camera 30, and the resulting image information is supplied to the calculator 20. In the calculator 20, the coordinate position of the bright spot SP on the chart 11 for measuring scanning characteristics is calculated using the input image information, and the result is stored in the storage 19.

Next, after performing step S403 in FIG. 4, an image of the chart 11 for measuring scanning characteristics having the bright spot SP illustrated in FIG. 6 is captured with the camera 30, and the resulting image information is supplied to the calculator 20. In the calculator 20, as described above, the coordinate position of the bright spot SP on the chart 11 for measuring scanning characteristics is calculated using the input image information, and the result is stored in the storage 19. The calculator 20 then calculates the angle of deviation with reference to the two coordinate positions stored in the storage 19 and the displacement distance L. As in Embodiment 2, the angle of deviation may be calculated on the basis of a formula that uses the distances $L_1$ and $L_2$ between the insertion tip 100*a* and the chart 11 for measuring scanning characteristics. The angle of deviation calculated by the calculator 20 is displayed on the display 14 and stored, as necessary, in the storage 109 of the scanning endoscope 100.

Subsequently, after performing steps S405 to S409 in FIG. 4, an image of the chart 11 for measuring scanning characteristics having the scanning area A from illumination light as illustrated in FIG. 10 is captured with the camera 30, and the resulting image information is supplied to the calculator 20. In the calculator 20, the viewing angle is calculated using the input image information, and the result is stored in the storage 19. The viewing angle calculated by the calculator 20 is displayed on the display 14 and stored, as necessary, in the storage 109 of the scanning endoscope 100. The drive signal information obtained by executing steps S405 to S408 is stored in the storage 19 and transmitted, as necessary, to the storage 109 of the scanning endoscope 100.

According to this embodiment, the angle of deviation and the viewing angle of the scanning endoscope 100 are calculated automatically by calculation processing, thereby allowing highly accurate measurement of the angle of deviation and the viewing angle.

This disclosure is not limited to the above embodiments, and a variety of changes or modifications may be made. For example, in Embodiment 3, the calculator 20 of the measurement apparatus body 10 may be omitted, and the image captured by the camera 30 may be processed by the controller 16 and displayed on the display 14. In this case, the image captured by the camera 30 can be expanded and displayed on the display 14, allowing an improvement in the measurement accuracy of the angle of deviation and the viewing angle. The observation apparatus body connected when the scanning endoscope 100 is used can also be provided with the functions of the measurement apparatus body 10. In this way, before the scanning endoscope 100 is used, the user can learn the angle of deviation and the viewing angle and can appropriately calibrate the drive signal.

The scanning characteristics are not limited to the case of measuring both the angle of deviation and the viewing angle. Only one of these may be measured instead. The angle of deviation can also be calculated using i) the distance between the center of the scanning area A illustrated in FIG. 9 and formed by step S408 in FIG. 4 and the center of the viewing angle index patterns 11a and ii) the separation distance L between the insertion tip 100a and the chart 11 for measuring scanning characteristics.

Figure 14:
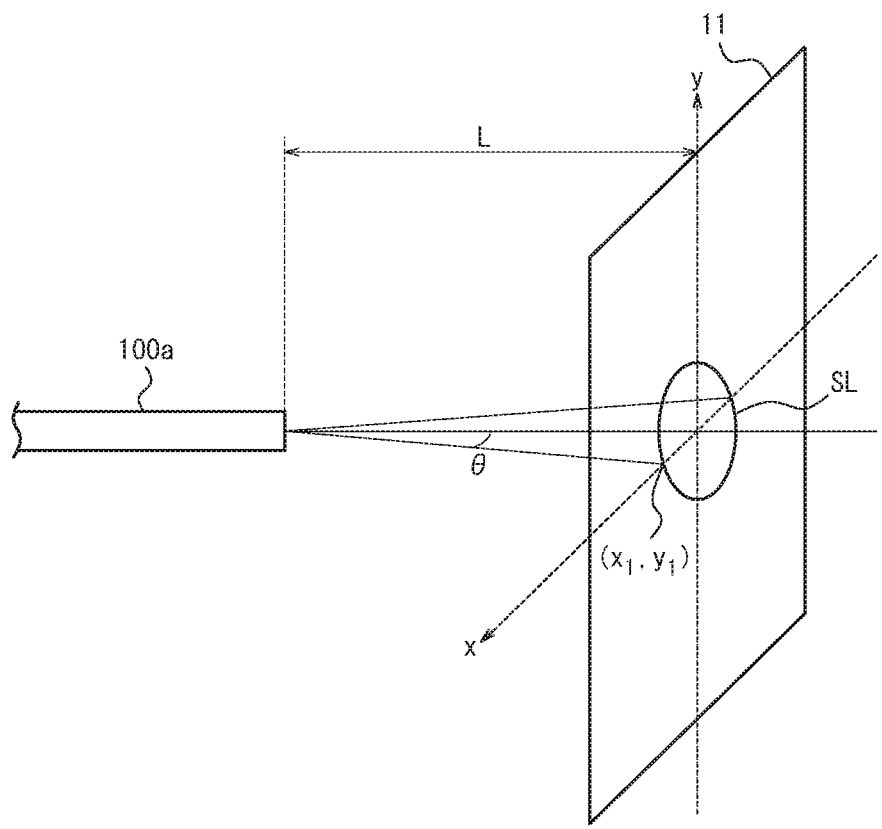
FIG. 14 illustrates another example of a method of measuring the angle of deviation with the chart for measuring scanning characteristics in FIG. 11.

In the case of using the chart 11 for measuring scanning characteristics that has the coordinate index pattern 11d illustrated in FIG. 11, the angle of deviation θ can be measured as illustrated in FIG. 14. In other words, as illustrated in FIG. 14, the insertion tip 100a and the chart 11 for measuring scanning characteristics are separated by a distance L, the actuator 103 is placed in a non-driven state, and the insertion tip 100a is rotated around the z-axis to form a circular scanning trajectory SL on the chart 11 for measuring scanning characteristics. The center (origin) of the coordinate index pattern 11d preferably matches the bright spot of the illumination light irradiated from the insertion tip 100a when the insertion tip 100a is nearby. The angle of deviation θ is then measured using the distance L and the coordinate position $(x_1, y_1)$ on the circular scanning trajectory SL farthest from the origin of the coordinate index pattern 11d.

Figure 15:
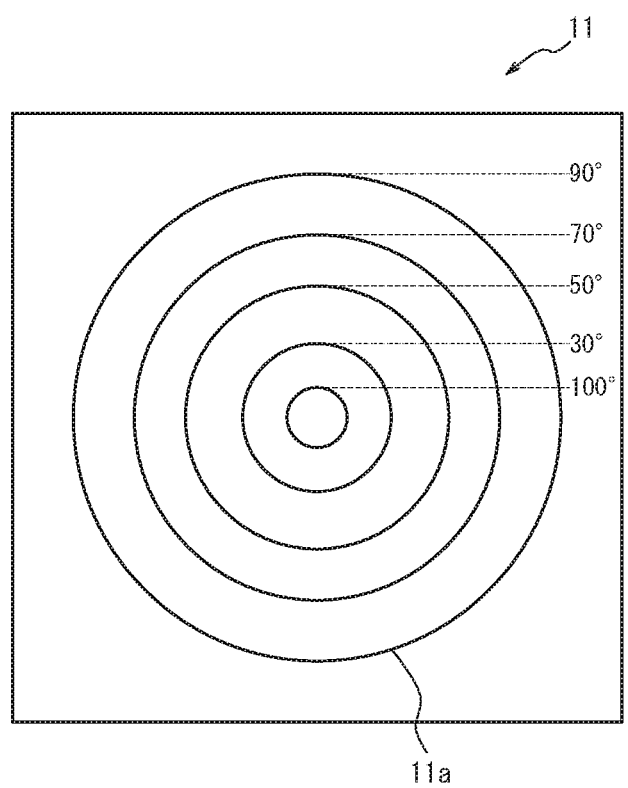
FIG. 15 is a plan view schematically illustrating a modification to the chart for measuring scanning characteristics.
Figure 16:
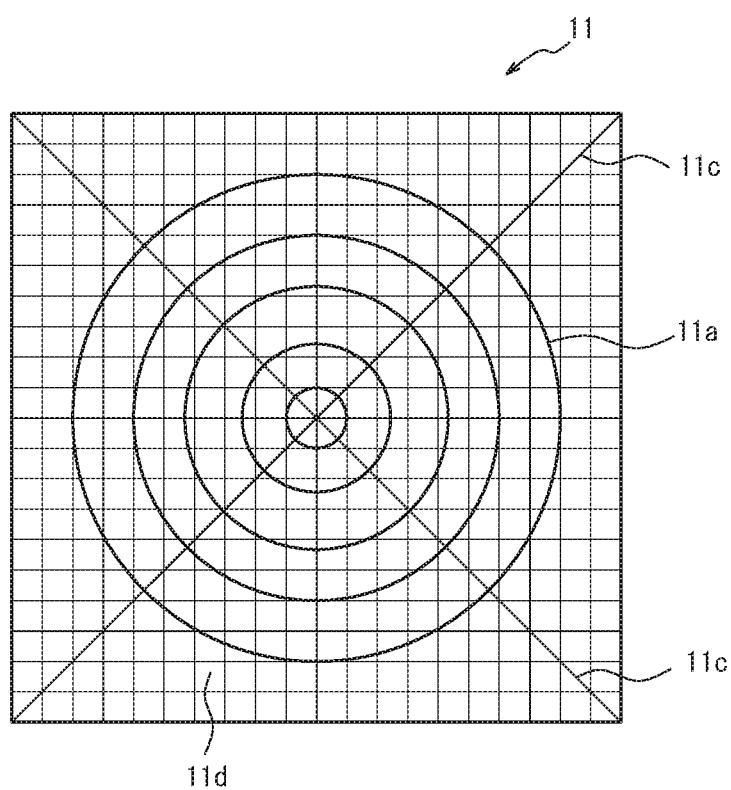
FIG. 16 is a plan view schematically illustrating another modification to the chart for measuring scanning characteristics.

The chart 11 for measuring scanning characteristics is not limited to the configurations illustrated in FIG. 2 and FIG. 11 and may instead have only the viewing angle index patterns 11a as illustrated in the schematic plan view in FIG. 15, or may include diagonals 11c in addition to the viewing angle index patterns 11a and the coordinate index pattern 11d as illustrated in the schematic plan view in FIG. 16. The scanning endoscope 100 targeted for measurement is not limited to spiral scanning, and the angle of deviation and viewing angle can be measured similarly for a scanning endoscope that performs a raster scan or Lissajous scan. In this case, use of a chart such as the chart 11 for measuring scanning characteristics illustrated in FIG. 16 is particularly preferable. The viewing angle index patterns 11a of the chart 11 for measuring scanning characteristics are not limited to being concentric circles and may have any shapes, such as concentric rectangles or ellipses, in accordance with the form of scanning.

Figure 17:
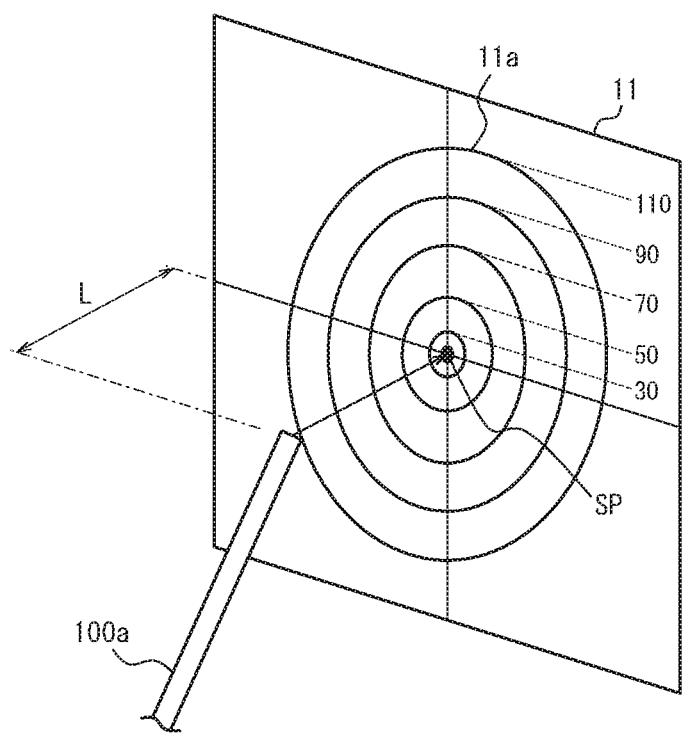
FIG. 17 illustrates a modification to a method of measuring scanning characteristics.

In the description in FIG. 4, the insertion tip 100a of the scanning endoscope 100 extends in the z-direction and is held on the Z stage 12, but this configuration is not limiting. For example, as in the exaggerated view in FIG. 17, the insertion tip 100a may be held so that the emission direction of illumination light emitted from the insertion tip 100a when the actuator 103 is not being driven (the optical axis direction) can be in the z-direction passing through the center of the viewing angle index patterns 11a of the chart 11 for measuring scanning characteristics. In this case, the angle of deviation can, for example, be measured as the inclination of the insertion tip 100a relative to the normal direction of the chart 11 for measuring scanning characteristics. The viewing angle can be measured by executing steps S405 to S410 in FIG. 4. In this case, the processing in step S409 may be omitted, since a scanning area with good circularity is obtained. Even when adjusting to the state in FIG. 17, however, the processing in step S409 is preferably executed, since the center of the scanning area in the scanning state might deviate from the center of the viewing angle index patterns 11a. Note that FIG. 17 illustrates the insertion tip 100a as being separated from the chart 11 for measuring scanning characteristics by a distance L.

The actuator 103 of the scanning endoscope 100 is not limited to a piezoelectric method and may instead adopt another known driving method, such as a MEMS mirror or an electromagnetic method that uses coils and a permanent magnet. Furthermore, this disclosure is not limited to measuring the scanning characteristics of a scanning endoscope and is also applicable to measuring the scanning characteristics of a scanning microscope.

The invention claimed is:

1. A method of measuring scanning characteristics of an optical scanning apparatus that drives an actuator and scans illumination light in two dimensions, the method comprising:
    a first step, with the actuator in a non-driven state, of bringing a tip, that emits the illumination light, of the optical scanning apparatus and a chart for measuring scanning characteristics closer together and irradiating the chart for measuring scanning characteristics with the illumination light;
    a second step of separating the tip and the chart for measuring scanning characteristics by a predetermined distance while maintaining relative orientations of the tip and the chart for measuring scanning characteristics from the first step; and
    a third step of adjusting a drive signal of the actuator so that a scanning area of the illumination light on the chart for measuring scanning characteristics can form a desired shape, wherein at least one of an angle of deviation and a viewing angle is measured using an irradiation position of the illumination light on the chart for measuring scanning characteristics, wherein the illumination light is emitted from an optical fiber, wherein the actuator vibrates an emission end of the optical fiber in an x-direction and a y-direction both orthogonal to an extending direction of the emission end and scans the illumination light in two dimensions, and wherein the third step adjusts a frequency, an amplitude, and a phase difference of an X drive signal that drives the actuator in the x-direction and a Y drive signal that drives the actuator in the y-direction.

2. The method according to claim 1, wherein the chart for measuring scanning characteristics includes concentric viewing angle index patterns, and wherein the third step adjusts the X drive signal and the Y drive signal so that a scanning trajectory of the illumination light can be inscribed in a desired one of the viewing angle index patterns.

3. The method according to claim 2, wherein after the first step, a bright spot of the illumination light is placed substantially at a center of the viewing angle index patterns before the second step, and wherein after the second step, the angle of deviation is measured using the viewing angle index patterns and the bright spot of the illumination light positioned on the chart for measuring scanning characteristics.

4. The method according to claim 2, wherein the viewing angle is measured using the viewing angle index patterns.

5. The method according to claim 4, further comprising:

a fourth step, after the third step, of substantially matching a center of the scanning area of the illumination light to a center of the viewing angle index patterns of the chart for measuring scanning characteristics, wherein in the fourth step, the viewing angle is measured using the viewing angle index patterns.

6. The method according to claim 1, wherein the chart for measuring scanning characteristics is imaged by an imaging apparatus and displayed on a display.

7. The method according to claim 1, wherein the chart for measuring scanning characteristics is imaged by an imaging apparatus, and the scanning characteristics are calculated automatically by a calculator using image information obtained from the imaging apparatus.

8. The method according to claim 1, wherein the optical scanning apparatus is a scanning endoscope.

9. A method of measuring scanning characteristics of an optical scanning apparatus that drives an actuator and scans illumination light in two dimensions, the method comprising:

a first step, with the actuator in a non-driven state, of bringing a tip, that emits the illumination light, of the optical scanning apparatus and a chart for measuring scanning characteristics closer together and irradiating the chart for measuring scanning characteristics with the illumination light;

a second step of separating the tip and the chart for measuring scanning characteristics by a predetermined distance while maintaining relative orientations of the tip and the chart for measuring scanning characteristics from the first step; and a third step of adjusting a drive signal of the actuator so that a scanning area of the illumination light on the chart for measuring scanning characteristics can form a desired shape, wherein at least one of an angle of deviation and a viewing angle is measured using an irradiation position of the illumination light on the chart for measuring scanning characteristics, wherein the chart for measuring scanning characteristics includes a coordinate index pattern indicating coordinate positions, and wherein the angle of deviation is measured using the following equation, $$\theta = \arctan\left(\frac{\sqrt{(x_2 - x_1)^2 + (y_2 - y_1)^2}}{|L_2 - L_1|}\right)$$

where a distance between the tip of the optical scanning apparatus and the chart for measuring scanning characteristics is $L_1$ and a coordinate position of a bright spot of the illumination light on the chart for measuring scanning characteristics is $(x_1, y_1)$ in the first step, and where a distance between the tip of the optical scanning apparatus and the chart for measuring scanning characteristics is $L_2$ and a coordinate position of a bright spot of the illumination light on the chart for measuring scanning characteristics is $(x_2, y_2)$ in the second step.

* * * * *